(12) United States Patent
Gavalis et al.

(10) Patent No.: US 10,660,506 B2
(45) Date of Patent: May 26, 2020

(54) ADJUSTABLE ENDOSCOPIC LOCKS

(71) Applicant: HOYA Corporation, Tokyo (JP)

(72) Inventors: Robb Morse Gavalis, Westborough, MA (US); Christopher Kadamus, West Roxbury, MA (US); Hrishikesh Vishvas Deo, Brooklyn, NY (US); Nicholas H. Tran, Revere, MA (US)

(73) Assignee: HOYA CORPORATION, Tokyo (JP)

( * ) Notice: Subject to any disclaimer, the term of this patent is extended or adjusted under 35 U.S.C. 154(b) by 496 days.

(21) Appl. No.: 15/584,844

(22) Filed: May 2, 2017

(65) Prior Publication Data

US 2018/0317750 A1 Nov. 8, 2018

(51) Int. Cl.
*A61B 1/00* (2006.01)

(52) U.S. Cl.
CPC ...... *A61B 1/00066* (2013.01); *A61B 1/00112* (2013.01); *A61B 1/00121* (2013.01); *A61B 1/00128* (2013.01); *A61B 1/00002* (2013.01); *A61B 1/00131* (2013.01); *A61B 1/00149* (2013.01)

(58) Field of Classification Search
None
See application file for complete search history.

(56) References Cited

U.S. PATENT DOCUMENTS

| | | | |
|---|---|---|---|
| 5,501,698 A * | 3/1996 | Roth | A61B 17/1285 606/174 |
| 8,597,242 B2 | 12/2013 | Fink | |
| 2007/0270640 A1 * | 11/2007 | Dimitriou | A61B 1/00128 600/106 |
| 2015/0073211 A1 * | 3/2015 | Dickhans | A61B 1/0014 600/104 |
| 2016/0166330 A1 * | 6/2016 | Lawrence | A61B 17/3468 606/116 |

FOREIGN PATENT DOCUMENTS

| CN | 107 669 353 A | 2/2018 |
|---|---|---|
| WO | WO 2015/052320 A1 | 4/2015 |

OTHER PUBLICATIONS

International Search Report for International Application No. PCT/IB2018/000541 filed May 1, 2018, dated Sep. 25, 2018, 13 pages.

* cited by examiner

*Primary Examiner* — Timothy J Neal
(74) *Attorney, Agent, or Firm* — Finnegan, Henderson, Farabow, Garrett & Dunner, L.L.P.

(57) ABSTRACT

Embodiments of the present disclosure are directed to apparatuses, devices, and methods for locks for endoscopic accessories. In one implementation, an adjustable lock for an endoscopic accessory includes a body slidably mounted upon a rail of the endoscopic accessory, and an arm extending about a portion of the body. The arm may be connected to the body and pivotable relative to the body between a closed position and an open position. In the closed position, teeth on an inner surface of the arm may engage a toothed rack on the rail such that the adjustable lock is secured to the rail. In the open position, the teeth on the inner surface of the arm may be clear of the toothed rack such that the lock may slide relative to the rail.

24 Claims, 8 Drawing Sheets

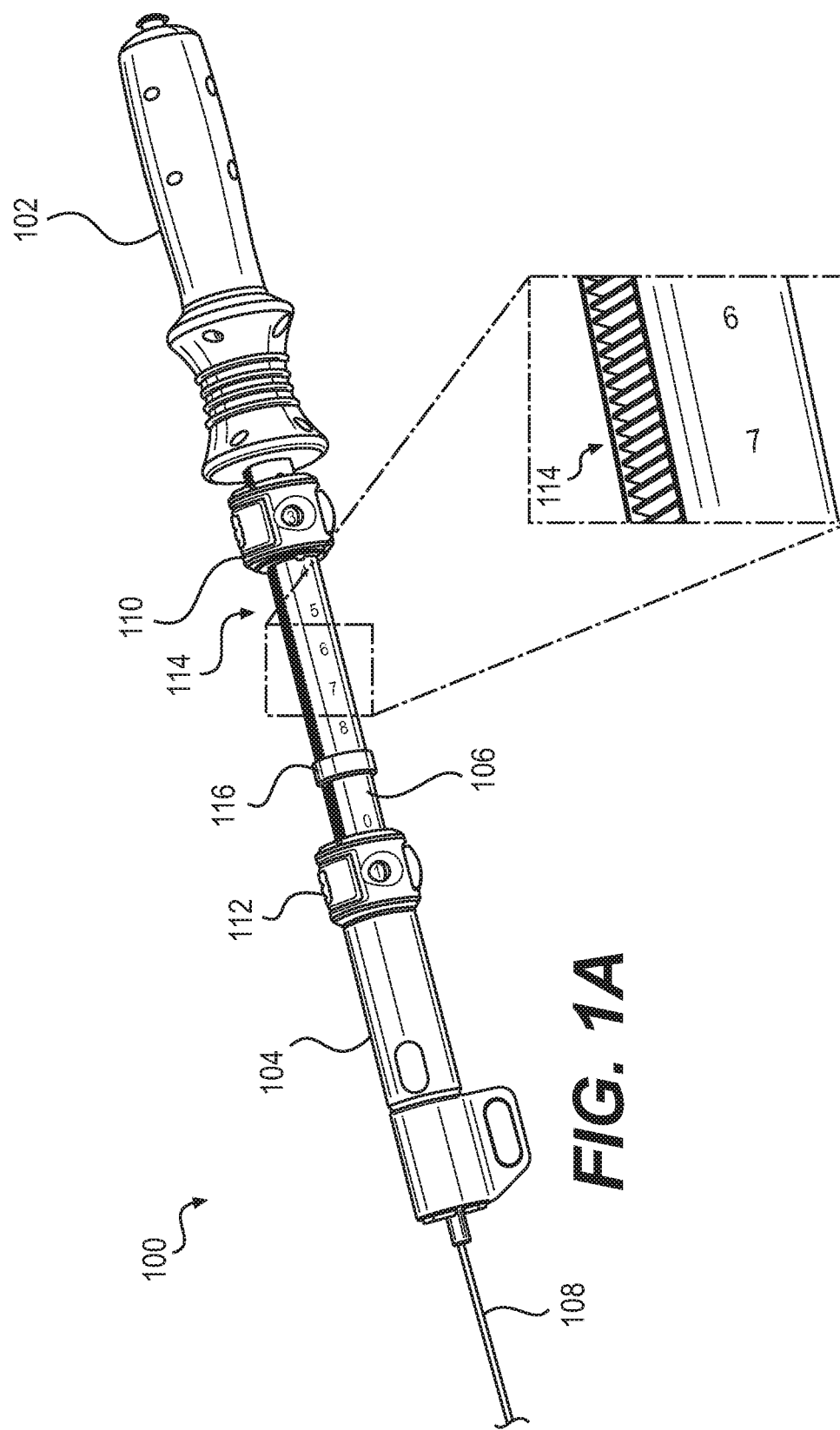
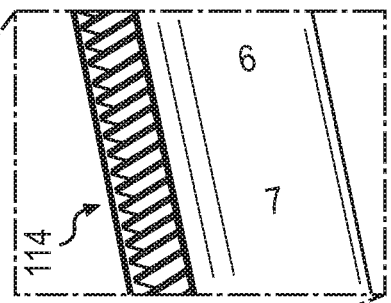
FIG. 1A
FIG. 1B

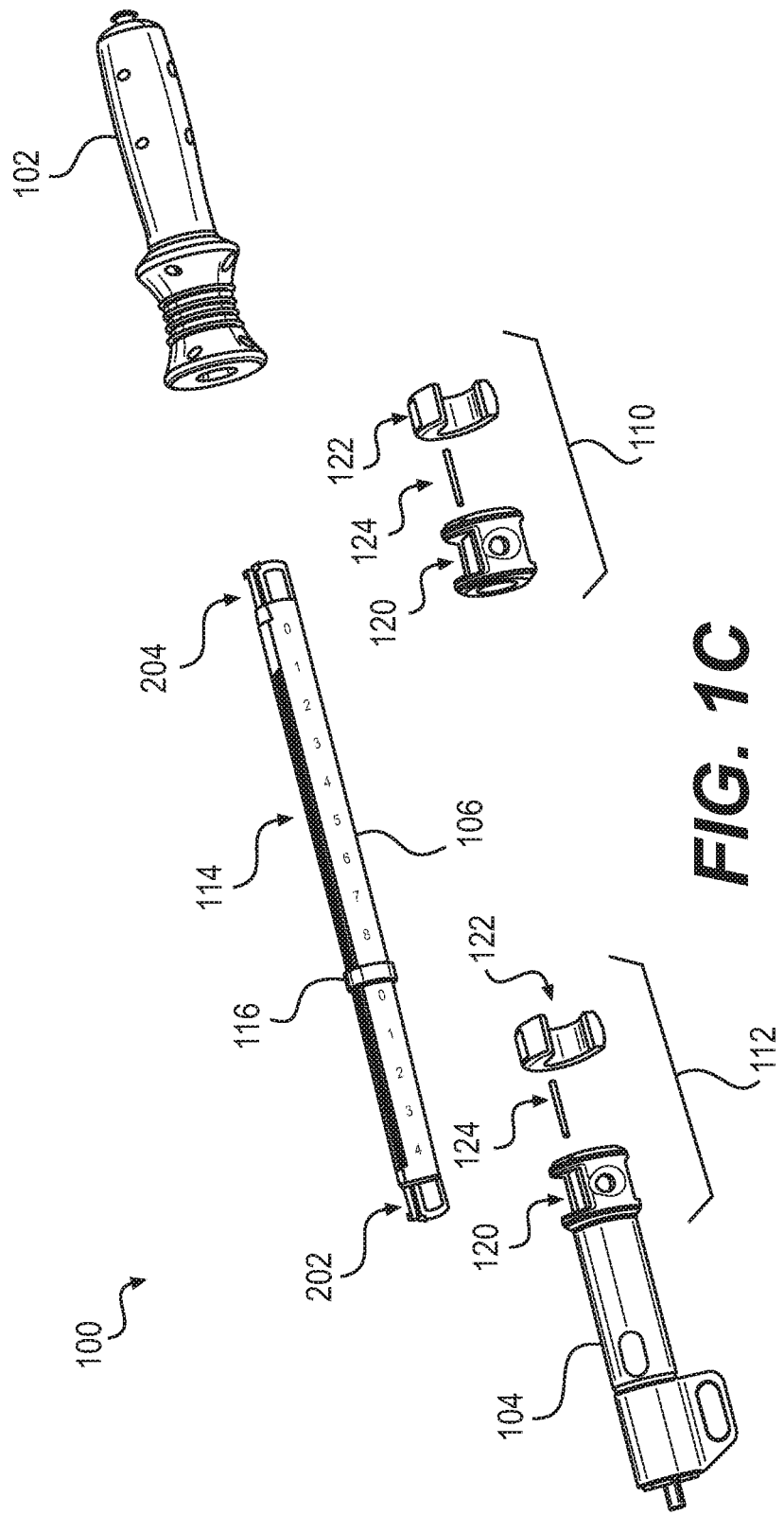

ADJUSTABLE ENDOSCOPIC LOCKS

BACKGROUND

Technical Field

The present disclosure generally relates to endoscopic accessories and methods of use. More particularly, and without limitation, the disclosed embodiments relate to apparatuses, systems, and methods for adjustable locks for endoscopic accessories.

Background Description

Endoscopic procedures often require the introduction of an accessory through the internal working channel of an endoscope for delivery to a desired diagnosis or treatment site. For example, in an endoscopic ultrasound (EUS) procedure, an endoscope with an ultrasonic transducer mounted on its distal end may be introduced into the body to collect images of internal body structures. EUS procedures are often combined with fine needle aspiration (FNA) or fine needle biopsy (FNB) procedures, during which a needle may be introduced through the working channel of the endoscope until it protrudes from the distal tip of the endoscope. Under ultrasonic guidance, the needle may be used to collect samples from the internal body structures.

Endoscopic needles and other endoscopic accessories often include a handle and a flexible sheath. The handle may be attached to the proximal end of the accessory and may be used to guide introduction of the accessory through the working channel as well as to control the accessory during endoscopic procedures. The flexible sheath may house and enclose the accessory, protecting the accessory and the endoscope during introduction of the accessory through the working channel. In many cases, the handle may include a feature for controlling relative movements of the accessory and the flexible sheath.

Prior endoscopic accessory handles have included a rail component with a proximal handle component and a distal handle component mounted upon it. The proximal handle component and the distal handle component slide longitudinally along the rail. The proximal handle component is attached to the accessory (e.g. a needle) and is utilized by the physician to control movement of the accessory. The distal handle component is utilized to control the length of the flexible sheath which extends from the distal end of the accessory handle. Some prior endoscopic accessory handles have additionally included two or more locks, which slide along the rail when unlocked and which are secured to the rail when locked. One lock is connected to the distal handle component and is used to lock the distal handle component to the rail, thus setting the flexible sheath length for the duration of the endoscopic procedure. Often, the physician will set the flexible sheath length at the beginning of the procedure to accommodate the brand and model of endoscope being utilized during the procedure. The second lock is used to limit the maximum depth of the accessory. During the procedure, the physician will unlock the second lock and move it to a location upon the rail corresponding to the maximum depth the proximal handle component and the accessory should be allowed to move, and will then lock the second lock at that location.

Some prior locks have utilized thumbscrews to secure the locks to the rail. The thumbscrews extend outwards from the side of the accessory handle and may be loosened to allow movement of the locks and tightened to secure the lock to the rail. However, these prior locks present a number of problems. The thumbscrews do not have defined locked and unlocked positions; as a result, it is difficult to determine when the lock is sufficiently tightened so as to prevent movement of accessory handle components during endoscopic procedures. This may result in inadvertent movement of components during a procedure due to insufficient tightening of one or more locks. Additionally, a physician may excessively tighten a lock, potentially damaging the accessory and the accessory handle or making it difficult for the physician to release and reposition the lock. Further, because the thumbscrews protrude from the side of the accessory handle, they may interfere with or be an inconvenience to the physician during use. For example, the physician may need to adjust from their ideal grip on the device to accommodate the thumbscrews.

Therefore, improved adjustable locks are needed to have a low profile and to indicate to the physician when they are locked and unlocked, while still maintaining a strong, secure connection when locked. Such improved adjustable locks may be capable of providing clear feedback when in the locked and unlocked positions such that the physician may have confidence about the lock being secured. Such improved adjustable locks may also have a low profile, thereby reducing or minimizing inconvenience to the physician during handling of the endoscopic accessory.

SUMMARY

The embodiments of the present disclosure include apparatuses, systems, and methods for locks for endoscopic accessories. Advantageously, the exemplary embodiments enable adjustably locking accessory components to an endoscopic accessory handle using locks which are low-profile, sturdy, and easily operated with one hand.

According to an exemplary embodiment of the present disclosure, an adjustable lock for an endoscopic accessory is described. The lock includes a body slidably mounted on a rail of the endoscope accessory, the rail having a toothed rack extending in the longitudinal direction thereof. The lock additionally includes an arm extending about a portion of the body. The arm is connected to the body and pivotable relative to the body between a closed position and an open position. The arm includes teeth on an inner surface thereof. In the closed position, the teeth of the arm engage teeth of the toothed rack such that relative longitudinal movement between the lock and the rail is prevented. In the open position, the arm extends away from the body such that the teeth of the arm are clear of the teeth of the toothed rack, allowing the lock to slide relative to the rail.

According to a further exemplary embodiment of the present disclosure, an endoscopic accessory is described. The accessory includes a rail having a toothed rack extending in the longitudinal direction thereof. The accessory additionally includes a handle mounted upon the proximal end of the rail, the handle being connected to a tool. The accessory further includes a first adjustable lock. The first adjustable lock includes a first body slidably mounted on the rail. The first adjustable lock additionally includes a first arm extending about a portion of the first body. The first arm is connected to the first body and pivotable relative to the first body between a closed position and an open position. The first arm comprises teeth on an inner surface thereof. In the closed position, the teeth of the first arm engage teeth of the toothed rack such that relative longitudinal movement between the first lock and the rail is prevented. In the open position, the first arm extends away from the first body such that the teeth of the first arm are clear of the teeth of the toothed rack, allowing the first lock to slide relative to the rail.

Additional features and advantages of the disclosed embodiments will be set forth in part in the description that follows, and in part will be obvious from the description, or may be learned by practice of the disclosed embodiments. The features and advantages of the disclosed embodiments will be realized and attained by the elements and combinations particularly pointed out in the appended claims.

It is to be understood that both the foregoing general description and the following detailed description are examples and explanatory only and are not restrictive of the disclosed embodiments as claimed.

The accompanying drawings constitute a part of this specification. The drawings illustrate several embodiments of the present disclosure and, together with the description, serve to explain the principles of the disclosed embodiments as set forth in the accompanying claims.

BRIEF DESCRIPTION OF THE DRAWINGS

FIG. 1A is a perspective view of an exemplary endoscopic accessory handle, according to embodiments of the present disclosure.

FIG. 1B is a close-up view of an exemplary rail of the exemplary endoscopic accessory handle of FIG. 1A, according to embodiments of the present disclosure.

FIG. 1C is a component view of the exemplary endoscopic accessory handle of FIG. 1A, according to embodiments of the present disclosure.

DETAILED DESCRIPTION

Figure 2A:
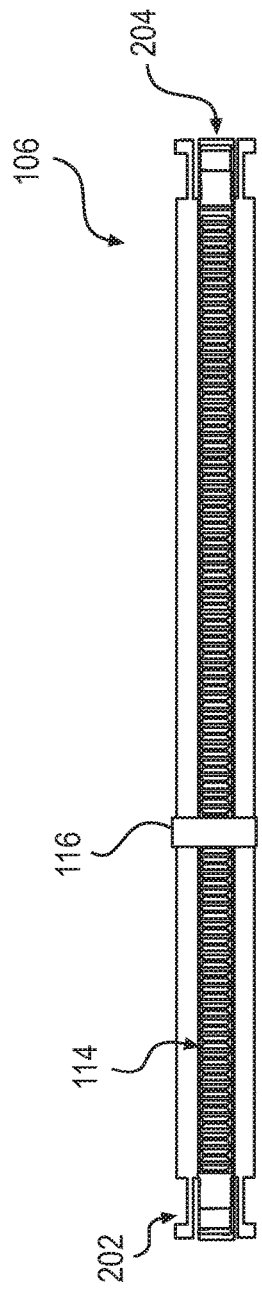
FIG. 2A is a top plan view of the exemplary rail of the exemplary endoscopic accessory handle of FIG. 1A, according to embodiments of the present disclosure.

Various disclosed embodiments relate to systems, apparatuses, and methods for controlled adjustment of components within an endoscopic accessory handle. Embodiments of the present disclosure may be implemented with the handle of an endoscopic needle for performing biological sample collection operations, such as fine needle biopsy (FNB) and fine needle aspiration (FNA). Embodiments of the present disclosure may also be implemented with an endoscope system for performing diagnostic and/or therapeutic operations, such as Endoscopic Ultrasound (EUS) procedures. However, it will be appreciated that embodiments of the present disclosure are not limited to FNB, FNA, or EUS, and that the systems, apparatuses, and methods disclosed herein may be implemented with any suitable endoscopic accessory or within any suitable diagnostic or therapeutic system.

As described herein, an endoscope typically includes a proximal end and a distal end, and has one or more internal lumens extending between the distal end and the proximal end. A proximal end may refer to a point or a location along the length of the endoscope closer to a physician or a medical practitioner. A distal end may refer to a point or location along the length of the endoscope closer to a diagnosis or treatment site in the body of a patient during an endoscopic procedure. In some cases, the distal end may include a tool for diagnosis or treatment, such as an ultrasonic transducer. One of the internal lumens of the endoscope may serve as a working channel to introduce an endoscopic accessory into the endoscope until a distal end of the accessory approximates or reaches a desired diagnosis or treatment site at the distal end of the endoscope. Examples of endoscopic accessories may include biopsy needles, aspiration needles, cannulae, sphincterotomes, balloons, baskets, brushes, and forceps. The working channel may have a biopsy port at its proximal end into which the accessory may be introduced. As described herein, the longitudinal axis of a given channel or tubular structure may refer to a central axis or an off-center axis of the channel or tubular structure.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used herein and in the appended claims, the singular forms "a," "an," and "the" include plural references unless the context clearly dictates otherwise.

FIG. 1A is a perspective view of an exemplary endoscopic accessory handle 100. Accessory handle 100 may be connected to any desired endoscopic accessory and may be used to control movement and operation of the accessory. Exemplary endoscopic accessories may include, and are not limited to, needles, cannulae, sphincterotomes, balloons, baskets, brushes, and forceps. In some embodiments, accessory handle 100 may be connected to an FNA needle or an FNB needle for controlled movement and operation thereof. A flexible sheath 108 may extend from the distal end of accessory handle 100. One of ordinary skill in the art will understand the term "flexible" to mean sheath 108 is capable of bending without breaking or fracture. This capability may be due, at least in part, to the material composition of sheath 108. For example, sheath 108 may be constructed of a flexible material such as PTFE, PEEK, or a composition of flexible materials. In some embodiments, sheath 108 is sufficiently flexible so as to be inserted through a tortuous endoscopic working channel without fracturing or being damaged. In some embodiments, the endoscopic accessory may be at least partially inserted into sheath 108 such that sheath 108 may house and protect the accessory.

Accessory handle 100 may include rail 106, which may extend in a direction parallel to the longitudinal axis of handle 100. An internal device handle 102 and a sheath length adjustment handle 104 may be at least partially mounted upon the proximal end and the distal end, respectively, of rail 106 and may be configured to slide longitudinally along rail 106. Sheath 108 may be secured to rail 106 and may extend distally from the distal end of rail 106. Sheath length adjustment handle 104 may be mounted upon rail 106 so as to extend over at least a portion of sheath 108, with sheath 108 extending distally from the distal end of sheath length adjustment handle 104. Movement of sheath length adjustment handle 104 along rail 106 may adjust the length of the portion of sheath 108 which extends out from the distal end of accessory handle 100.

Internal device handle 102 may be connected to the endoscopic accessory and may be operated by the physician to actuate the endoscopic accessory. In some embodiments, a proximal end of the endoscopic accessory may be connected to internal device handle 102. The endoscopic accessory may extend through rail 106 and sheath 108 into a distal portion of sheath 108. Movement of internal device handle 102 relative to rail 106 may result in the endoscopic accessory protruding from the distal tip of sheath 108 and being retracted into sheath 108.

Accessory handle 100 may additionally include first adjustable lock 110 and second adjustable lock 112. First lock 110 and second lock 112 may extend about at least a portion of rail 106 and may be configured to slide relative to it. First lock 110 and second lock 112 may be configured to selectively lock and unlock to rail 106. In a locked configuration, first lock 110 and second lock 112 may be secured to rail 106 such that relative movement between them is prevented. In an unlocked configuration, first lock 110 and second lock 112 may slide relative to rail 106.

First lock 110 may be mounted upon rail 106 in proximity to internal device handle 102. In some embodiments, first lock 110 may be positioned between internal device handle 102 and the distal end of rail 106. Internal device handle 102 may slide along rail 106 between the proximal end of rail 106 and the locked position of first lock 110. Internal device handle 102 may not slide distally beyond the locked position of first lock 110 due to the locked arrangement between first lock 110 and rail 106, and because first lock 110 may be sufficiently large in diameter such that internal device handle 102 may not pass over first lock 110.

First lock 110 may serve as an actuation stop for internal device handle 102. The physician may lock first lock 110 at a position on rail 106 corresponding to the maximum desired actuation depth of the endoscopic accessory relative to sheath 108. Adjustment of first lock 110 in the distal direction along rail 106 allows internal device handle 102 to move further in the distal direction before it abuts first lock 110. As a result, the endoscopic accessory, which may be secured to internal device handle 102, may extend a greater distance from the distal tip of sheath 108. Conversely, adjustment of first lock 110 in the proximal direction along rail 106 reduces the possible distal movement of internal device handle 102, thereby reducing the maximum length of the endoscopic accessory which may extend from the distal tip of sheath 108.

Second lock 112 may be connected to the proximal end of sheath length adjustment handle 104. In some embodiments, the two may be manufactured together as a single structure. In some alternative embodiments, the two may be manufactured separately and secured together using known methods. Second lock 112 may be capable of locking and unlocking to rail 106 in a manner similar to first lock 110. Second lock 112 may also be capable of sliding relative to rail 106 when in an unlocked configuration. Because second lock 112 and sheath length adjustment handle 104 are secured together, they may slide together along rail 106 as a unitary structure when second lock 112 is unlocked. Conversely, when second lock 112 is locked to rail 106, second lock 112 and sheath length adjustment handle 104 are both prevented from moving relative to rail 106.

Second lock 112 may be used to secure the exposed length of sheath 108. For example, to increase an exposed length of sheath 108, second lock 112 may be unlocked and moved in the proximal direction along rail 106. When a desired exposed length of sheath 108 is reached, second lock 112 may be locked to rail 106, securing the position of sheath length adjustment handle 104 relative to sheath 108. Conversely, movement of second lock 112 in the distal direction may reduce the exposed length of sheath 108.

Rail 106 may additionally include barrier 116 in a middle portion thereof. In some embodiments, barrier 116 may be positioned in the middle of rail 106. In some alternative embodiments, barrier 116 may be positioned closer to the distal end of rail 106 than to the proximal end of rail 106. One of ordinary skill in the art will understand that barrier 116 may be positioned at any desired location upon rail 106. Barrier 116 may have an outer diameter which is larger than an inner diameter of first lock 110 and an inner diameter of second lock 112. As a result, first lock 110 and second lock 112 may not slide past barrier 116. In some embodiments, first lock 110 and internal device handle 102 may be positioned proximally of barrier 116, and second lock 112 and sheath length adjustment handle 104 may be positioned distally of barrier 116. According to these embodiments, barrier 116 may prevent first lock 110 and second lock 112 from sliding along the same portions of rail 106.

Accessory handle 100 may be used in conjunction with a diagnostic and/or therapeutic endoscope. According to some embodiments, sheath 108 may be introduced into the biopsy port of the endoscope and may be passed through the working channel until it extends out from the distal end of the endoscope at a diagnosis or treatment site within the patient's body. The distal end of sheath length adjustment handle 104 may be secured to the biopsy port to secure accessory handle 100 relative to the endoscope. In some embodiments, prior to introduction of the sheath, the physician may set the desired length of the exposed portion of sheath 108 by locking second lock 112 at the equivalent location on rail 106. The desired length may be set to correlate with, for example, the length of the working channel of the specific brand and model of endoscope being used. In this way, accessory handle 100 may be utilized with a variety of brands and models of endoscopes. In some instances, the physician may set the desired length of the exposed portion of sheath 108 at the beginning of the endoscopic procedure and may not change it for the remaining duration of the procedure.

Before, during, and/or after introduction of sheath 108 into the working channel, the physician may unlock, adjust, and relock first lock 110 to set the maximum actuation depth of the endoscopic accessory. In some embodiments, the physician may set the actuation depth after introduction of the sheath into the endoscope, and optionally may reset the actuation depth one or more times during the duration of the endoscopic procedure. By setting the location of first lock 110, the physician may control the maximum length of the endoscopic accessory which may extend out from the distal end of sheath 108.

The endoscopic accessory may be introduced through the working channel until it reaches a distal portion thereof. The physician may then actuate accessory handle 100 to cause extension of the endoscopic accessory out from the distal tip of sheath 108 and retraction of the endoscopic accessory into sheath 108. Sheath 108 may protect both the endoscopic accessory and the working channel of the endoscope. For example, sheath 108 may protect the endoscopic accessory during delivery of the accessory through the elevator of the endoscope, which may contain sharp turns.

FIG. 1B is a close-up view of an exemplary rail 106 of the exemplary endoscopic accessory handle 100. Rail 106 may have toothed rack 114 extending in the longitudinal direction thereof. Toothed rack 114 may contain a number of teeth. In some embodiments, toothed rack may not extend along the length of barrier 116, which may have a smooth outer surface. Accordingly, barrier 116 may separate a proximal portion and a distal portion of toothed rack 114.

FIG. 1C is a component view of the exemplary endoscopic accessory handle 100. Internal device handle 102 may have an opening at the distal end thereof sized to receive at least a proximal portion of rail 106. Sheath length adjustment handle 104 may have an opening on the proximal end thereof sized to receive at least a distal portion of rail 106.

First lock 110 and second lock 112 may each include a body 120, an arm 122, and a pivot pin 124. In some embodiments, first lock 110 and second lock 112 may be structurally identical other than the connection of second lock 112 to sheath length adjustment handle 104. Body 120 may be sized to receive rail 106 therein and to slide relative to rail 106. Arm 122 may be connected to body 120 via pivot pin 124. Pivot pin 124 may engage an end portion of arm 122 such that arm 122 may be configured to pivot relative to body 120 between an open position and a closed position. In the closed position, arm 122 may wrap around at least a portion of body 120. In the open position, arm 122 may extend away from body 120 such that arm 122 does not wrap around body 120.

Arm 122 may have teeth (not depicted in FIG. 1C) on an inner surface thereof which may engage the teeth of toothed rack 114. The teeth of arm 122 may form a toothed rack which extends in a direction parallel to toothed rack 114. The teeth of arm 122 and the teeth of toothed rack 114 may be the same size and/or shape such that when they engage, relative longitudinal movement between them may be prevented. In the closed position, arm 122 may be positioned such that toothed rack 114 engages the teeth on arm 122. Accordingly, the closed position may be the same position as the locked position of first lock 110 and of second lock 112 because relative longitudinal movement between arm 122 and rail 106 is prevented. In the open position, arm 122 may extend away from rail 106 such that toothed rack 114 is clear of the teeth on arm 122. Accordingly, the open position may be the same position as the unlocked position because when toothed rack 114 does not engage the teeth of arm 122, first lock 110 and/or second lock 112 are free to slide relative to rail 106.

FIG. 2A is a top plan view of exemplary rail 106. Rail 106 may include distal end portion 202 and proximal end portion 204. Distal end portion 202 may extend radially outwards beyond the outer surface of rail 106. In some embodiments, this extension may be larger in diameter than the internal diameter of body 120 of second lock 112. As a result, second lock 112 may be prevented from sliding distally past distal end portion 202. Proximal end portion 204 may similarly extend radially outwards beyond the outer surface of rail 106. Internal device handle 102 may have a lumen extending through at least a portion thereof; the diameter of the distal end of this lumen may be smaller than the outer diameter of proximal end portion 204 such that the distal end of internal device handle 102 may be prevented from sliding proximally past proximal end portion 204.

Figure 2B:
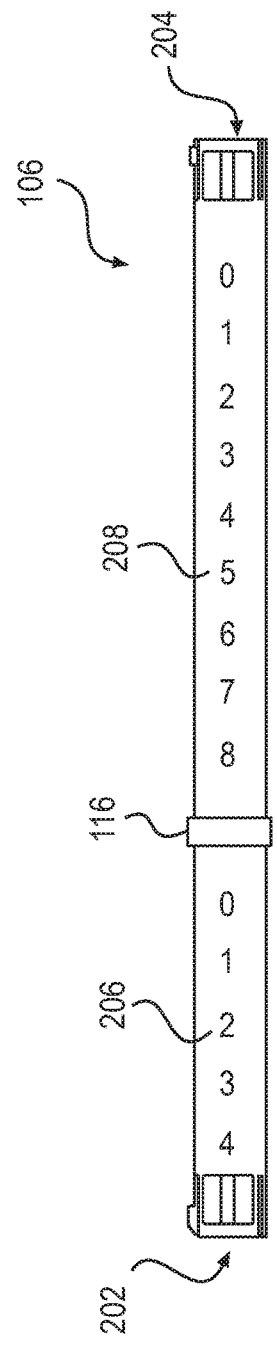
FIG. 2B is a side plan view of the exemplary rail of FIG. 2A, according to embodiments of the present disclosure.

FIG. 2B is a side plan view of exemplary rail 106. Rail 106 may include sheath length numbers 206 and internal device depth numbers 208. In some embodiments, sheath length numbers 206 may be positioned distally of barrier 116 and internal device depth numbers 208 may be positioned proximally of barrier 116. Body 120 of first lock 110 may contain a window through which internal device depth numbers 208 may be visible. Body 120 of second lock 112 may contain a window through which sheath length numbers 206 may be visible. In some embodiments, sheath length numbers 206 and internal device depth numbers 208 may be spaced every centimeter and may indicate the exposed length of sheath 108 and the maximum actuation depth of the endoscopic accessory, respectively.

Figure 2C:
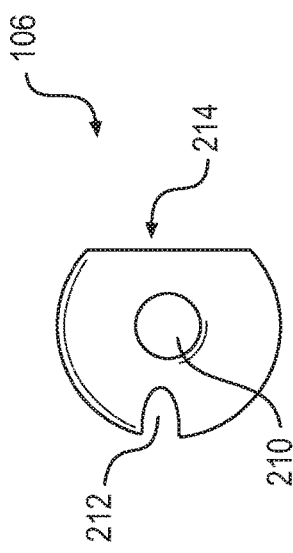
FIG. 2C is a cross-sectional view of the exemplary rail of FIG. 2A, according to embodiments of the present disclosure.

FIG. 2C is a cross-sectional view of exemplary rail 106. Rail 106 may include lumen 210 passing through a central portion thereof. Lumen 210 may be circular, oval-shaped, elliptical, or may have some other non-circular shape. Lumen 210 may extend along the entire longitudinal length of rail 106. In some embodiments, one or more of sheath 108 and the endoscopic accessory may extend through at least a portion of lumen 210. Rail 106 may additionally include trench 212, which may extend along the longitudinal axis of rail 106. In some embodiments, trench 212 may extend along the entire length of rail 106 except for a portion of rail 106 which is spanned by barrier 116. In some alternative embodiments, trench 212 may extend through barrier 116. Trench 212 may be sized to engage a rib mounted on body 120. Advantageously, trench 212 may assist in preventing relative rotational movement between rail 106 and body 120. Additionally, because trench 212 does not span barrier 116, first lock 110 and second lock 112 may be prevented from sliding past barrier 116.

Rail 106 may additionally include top surface 214. Top surface 214 may be flat and may extend along the entire length of rail 106 except for a portion of rail 106 which is spanned by barrier 116. Top surface 214 may extend radially inward from the outer-most surface of rail 106. The cross-section of rail 106 may be generally annular except for portions containing trench 212 and top surface 214. In some embodiments, trench 212 may be positioned directly opposite top surface 214; that is, trench 212 may be positioned 180° about the circumference of rail 106 from top surface 214.

Toothed rack 114 may extend along top surface 214. In some embodiments, toothed racked 114 may be formed by creating a series of grooves in the body of rail 106. As a result, toothed rack 114 does not extend radially outward beyond top surface 214. In some embodiments, the tops of the teeth of toothed racked 114 are substantially flush with top surface 214. In some alternative embodiments, the tops of the teeth of toothed racked 114 are positioned radially inward from top surface 214.

Figure 3A:
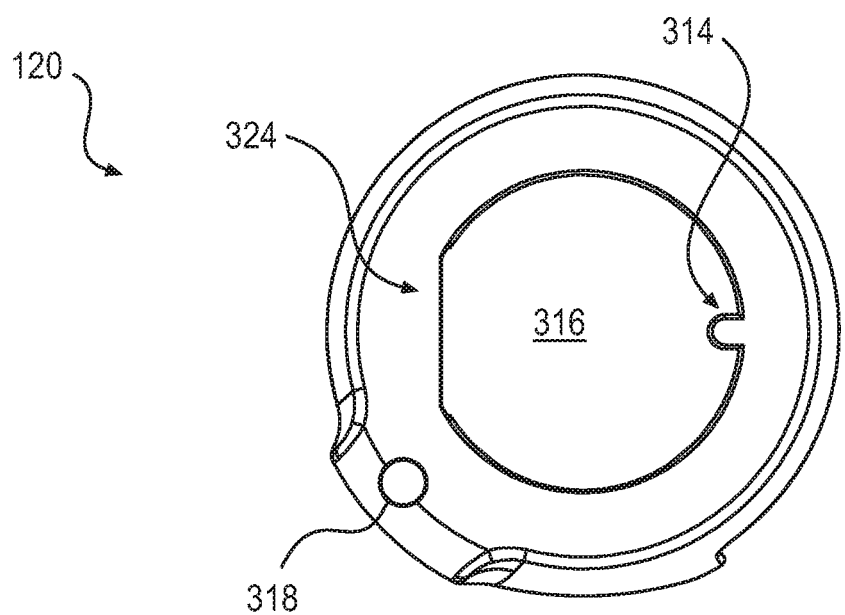
FIG. 3A is a view of an exemplary body of the exemplary endoscopic accessory handle of FIG. 1A, as viewed along the distal direction of the endoscopic accessory handle, according to embodiments of the present disclosure.

FIG. 3A is view of exemplary body 120 as viewed along the distal direction of accessory handle 100. Body 120 may include lumen 316 extending longitudinally therethrough. Lumen 316 may be sized to receive rail 106 therein. Body 120 may additionally include rib 314, which may be sized to be received within trench 212. The engagement of rib 314 and trench 212 may prevent relative rotational movement between rail 106 and body 120. Body 120 may additionally include body hole 318, which may be cylindrical and which may extend longitudinally along at least a portion of body 120. Body hole 318 may be sized to receive at least a portion of pivot pin 124 therein. In some embodiments, both ends of pivot pin 124 may be secured within body hole 318 by an adhesive. In some alternative embodiments, pivot pin 124 and body hole 318 are sized such that body 120 hugs both ends of pivot pin 124, preventing relative movement between them. In some embodiments, pivot pin 124 may be secured within body hole 318, and arm 122 may pivot relative to pivot pin 124 and body 120. In some alternative embodiments, pivot pin 124 may be secured to arm 122, and the two may pivot together relative to body 120. In some further alternative embodiments, pivot pin 124 may be configured to pivot relative to body 120 and to arm 122.

Body 120 may additionally include flat inner surface 324 extending along a portion of its inner diameter. In some embodiments, flat inner surface 324 may extend longitudinally along the entire length of body 120. In some embodiments, flat inner surface 324 may be positioned directly opposite rib 314 about a circumference of lumen 316. When rail 106 is received within body 120, top surface 214 may be positioned adjacent to flat inner surface 324. This proximity may assist in preventing relative rotational movement between body 120 and rail 106.

Figure 3B:
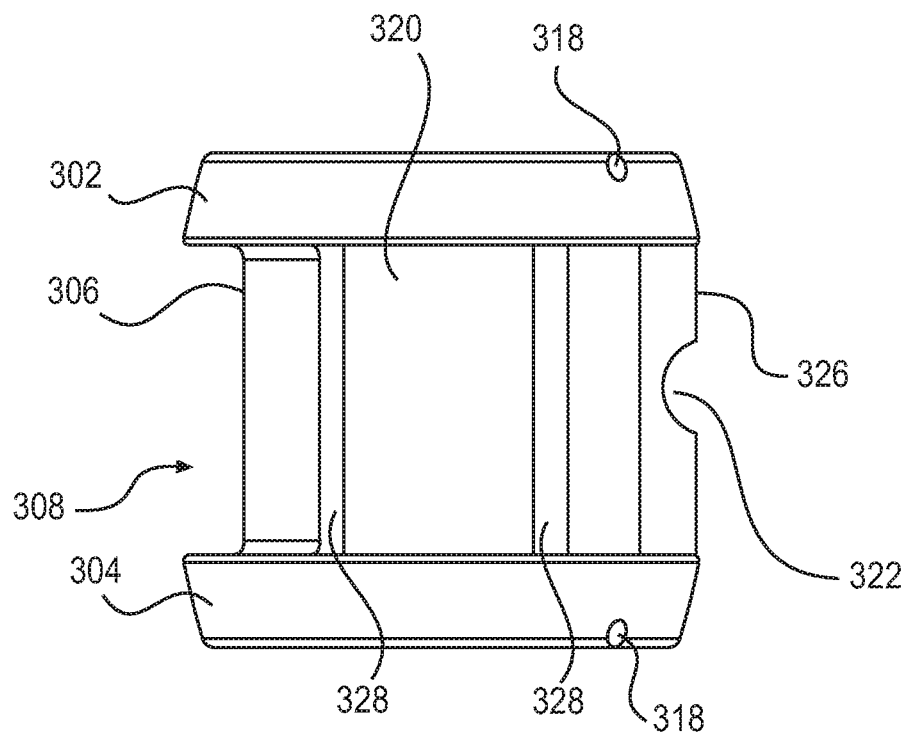
FIG. 3B is a side plan view of the exemplary body of FIG. 3A, according to embodiments of the present disclosure.

FIG. 3B is a side plan view of exemplary body 120. Body 120 may include proximal end portion 302 and distal end portion 304, with intermediate portion 306 extending between them. In some embodiments, when body 120 is mounted on rail 106, proximal end portion 302 may be the end of body 120 which is closest to the proximal end of rail 106; similarly, distal end portion 304 may be the end of body 120 which is closest to the distal end of rail 106. In some embodiments, proximal end portion 302 and distal end portion 304 may have outer surfaces which are equal in shape and diameter. A portion of the outer circumference of intermediate portion 306 may be positioned radially inwards from the outer surfaces of proximal end portion 302 and distal end portion 304. As a result, body 120 may additionally include a groove 308, which may extend around at least a portion of body 120. Groove 308 may be sized to receive arm 122 when arm 122 is in the closed position. Intermediate portion 306 may include border portion 326, which may be substantially even with the outer surfaces of proximal end portion 302 and distal end portion 304 such that groove 308 does not extend along border portion 326. A section of the wall forming intermediate portion 306 may be flat, forming flat wall portion 328. Flat inner surface 324 may span the inner surface of flat wall portion 328. In some embodiments, a middle portion of body hole 318 may be interrupted by groove 308 such that when pivot pin 124 is received within body hole 318, a portion of the pin may extend through groove 308.

Intermediate portion 306 may include opening 320 and window 322. Opening 320 may have a rectangular cross-section and may extend through a section of flat wall portion 328. In some embodiments, opening 320 may span the entire longitudinal length of intermediate portion 306. In some alternative embodiments, opening 320 may span a portion of the longitudinal length of intermediate portion 306.

Window 322 may have a circular cross-section. Window 322 may be positioned in border portion 326 and may be situated such that when body 120 is mounted on rail 106, sheath length numbers 206 and/or internal device depth numbers 208 may be visible through window 322. In some embodiments, window 322 may be positioned in a longitudinally central portion of intermediate portion 306.

Figure 3C:
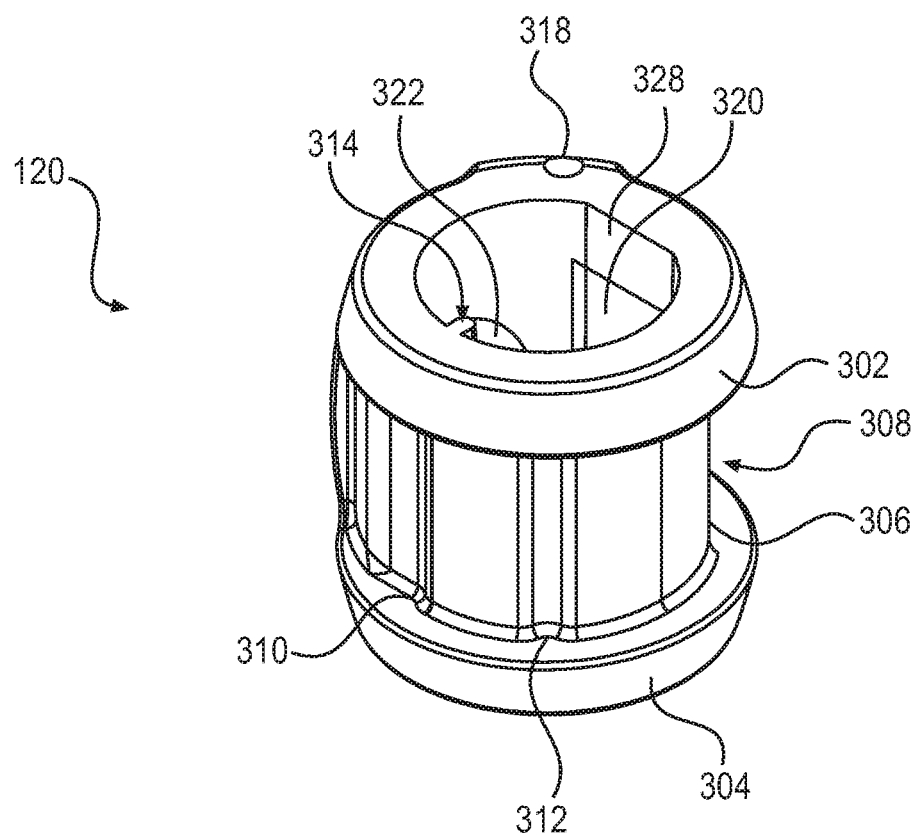
FIG. 3C is a perspective view of the exemplary body of FIG. 3A, according to embodiments of the present disclosure.

FIG. 3C is a perspective view of exemplary body 120. Intermediate portion 306 may additionally include one or more of closed position detent 310 and open position detent 312. In some embodiments, closed position detent 310 and open position detent 312 may be formed as depressions in the wall forming intermediate portion 306. In some embodiments, these depressions may longitudinally span the entire length of intermediate portion 306. In some alternative embodiments, these depressions may longitudinally span a portion of the length of intermediate portion 306. The depressions may have a profile which is semi-circular, rectangular, triangular, saw-toothed, or some other shape. Alternatively, the depressions may form a socket configured to receive a ball-shaped feature. Closed position detent 310 and open position detent 312 may be situated upon intermediate portion 306 such that they are positioned radially inwards from the outer surfaces of proximal end portion 302 and distal end portion 304.

Figure 3D:
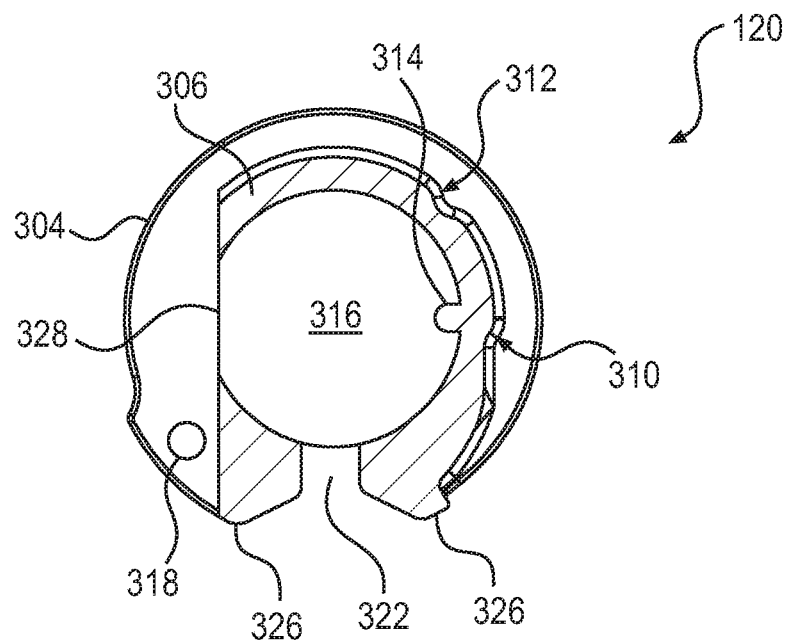
FIG. 3D is a cross-sectional view of the exemplary body of FIG. 3A, according to embodiments of the present disclosure.

FIG. 3D is a cross-sectional view of the exemplary body 120. In some embodiments, groove 308 may extend around intermediate portion 306 at an angle greater than 180°. That is, groove 308 may extend circumferentially around more than half of intermediate portion 306. As a result, in some embodiments border portion 326 may extend circumferentially around less than half of intermediate portion 306. In some embodiments, closed position detent 310 may be positioned between open position detent 312 and border portion 326.

Figure 4A:
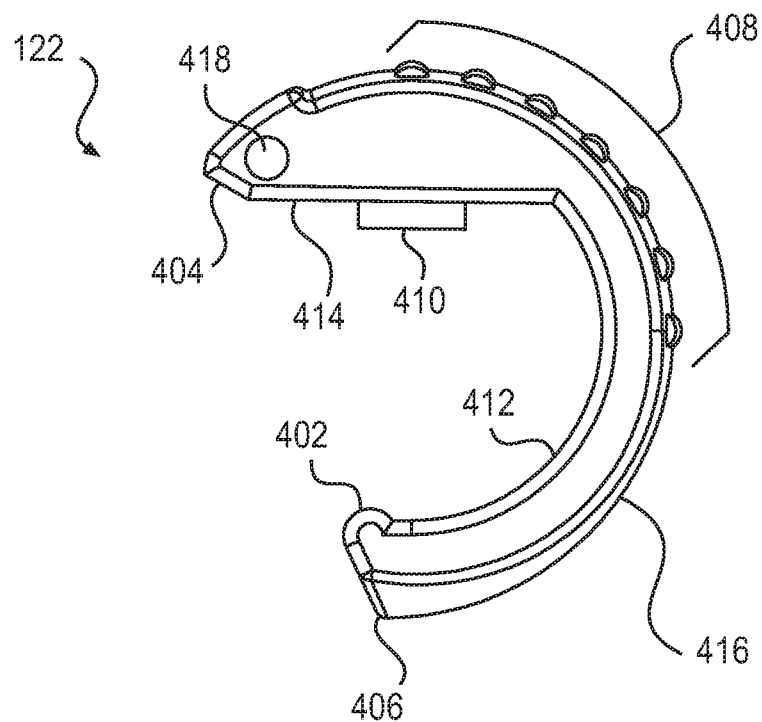
FIG. 4A is a view of an exemplary arm of the exemplary endoscopic accessory handle of FIG. 1A, as viewed along the distal direction of the endoscopic accessory handle, according to embodiments of the present disclosure.

FIG. 4A is view of an exemplary arm 122 as viewed along the distal direction of accessory handle 100. Arm 122 may be shaped to sit within groove 308 when in the closed position. Arm 122 may have an outer surface 416 and an inner surface including curved portion 412 and flat portion 414. Teeth 410 may be positioned upon flat portion 414 and may extend outwards from it. Teeth 410 may be formed as a toothed rack which may extend in a direction parallel to toothed rack 114. In some embodiments, arm 122 and teeth 410 may be manufactured as a unitary structure. In some alternative embodiments, arm 122 and teeth 410 may be manufactured separately, and teeth 410 may be secured to flat portion 414 using known methods.

Teeth 410 and the teeth of toothed rack 114 may engage each other by the insertion of the teeth of one into the inter-tooth gap of the other. Teeth 410 and the teeth of toothed rack 114 may engage, for example, when arm 122 is moved into the closed position. When engaged, the two sets of teeth may be fully flush such that there is no space between them. As a result, when the two sets of teeth engage, arm 122 and rail 106 may be completely secured against any relative longitudinal movements. In some embodiments, the two sets of teeth may have the same pitch. In some embodiments, the pitch is one tooth per a distance of between 0.5 millimeters and 5 millimeters. The pitch may be small enough to provide a large number of possible longitudinal positions of arm 122 relative to rail 106. This may provide the physician great flexibility in where they elect to position first lock 110 and second lock 112.

Teeth 410 and the teeth of toothed rack 114 may be triangular, saw-toothed, rectangular, square-shaped, rounded, ovular, or sinusoidal. In some embodiments, the two sets of teeth may be formed as isosceles triangles, with the side extending along the rack being shorter than the two sides extending outward from the rack. In some embodiments, if the physician closes arm 122 at a longitudinal position in which the two sets of teeth are not correctly aligned, the two sets of teeth may shift relative to each other until they reach a discrete position at which they are completely engaged. This may allow the physician to close arm 122 without any additional input and without having to visually confirm that the two sets of teeth are completely engaged.

Arm 122 may additionally include arm hole 418, which may be cylindrical and which may extend longitudinally along at least a portion of the length of arm 122. When arm 122 is secured to body 120 via pivot pin 124, arm hole 418 may be continuous with body hole 318 such that pivot pin 124 may extend through both. In some embodiments, arm hole 418 may be positioned between a proximal portion of body hole 318 and a distal portion of body hole 318. Arm 122 may pivot about body 120 at least between the open position and the closed position via pivot pin 124.

In some alternative embodiments, arm 122 may be connected to body 120 via a snap fit. Proximal end portion 302 and distal end portion 304 may include depressions in portions thereof. For example, the depressions may be positioned upon surfaces of proximal end portion 302 and distal end portion 304 which span intermediate portion 306. In these embodiments, in place of a pivot pin and pivot pin slot, arm 122 may include two projections which may be configured to sit within the depressions on proximal end portion 302 and distal end portion 304. Arm 122 may pivot relative to body 120 via the projections and depressions. The projections and depressions may form ball and socket joints, may be shaped as a rod and a matching cylinder, or may be shaped as a conical boss with a matching pocket.

In some further alternative embodiments, arm 122 may be connected to body 120 via a living hinge. Arm 122 and body 120 may be formed as a single unitary structure and may be connected by a thin flexible extension which may allow arm 122 to pivot at least between the open position and the closed position relative to body 120.

Curved portion 412 may be shaped to abut a portion of the outer surface of intermediate portion 306 when arm 122 is in the closed position. Similarly, flat portion 414 may be shaped to abut flat wall portion 328 and rail top surface 214 when arm 122 is in the closed position. Arm 122 may include hard stop 404 at one end thereof, in proximity to arm hole 418. Hard stop 404 may be angled relative to flat portion 414. Arm 122 may additionally include protrusion 402 on an end thereof opposite from arm hole 418 and/or hard stop 404. Protrusion 402 may be positioned upon curved portion 412 of the inner surface and may be shaped to sit within closed position detent 310 and open position detent 312. In some embodiments, protrusion 402 may extend longitudinally along the entire length of curved portion 412. One of ordinary skill in the art will understand the term "longitudinally" to refer to a direction parallel to the longitudinal axis of handle 100 when arm 122 is mounted thereon. In some alternative embodiments, protrusion 402 may extend longitudinally along a portion of the length of curved portion 412. Protrusion 402 may have a profile which is semi-circular, rectangular, triangular, saw-toothed, or some other shape. Alternatively, protrusion 402 may form a ball which is configured to be received and retained with a socket in body 120.

Arm 122 may be shaped such that when it is in the closed position, outer surface 416 is substantially even with outer surfaces of proximal end portion 302 and distal end portion 304 such that they form a smooth outer surface. Arm 122 may additionally include one or more of open touch point 406 and closed touch point 408 on outer surface 416. Open touch point 406 may be positioned at the same end of arm 122 as protrusion 402 and may extend radially outwards from outer surface 416. In some embodiments, when arm 122 is in the closed position, open touch point 406 may extend radially outwards beyond the smooth outer surface formed by proximal end portion 302, arm 122, and distal end portion 304. A physician may press on open touch point 406 to open the closed arm 122. Advantageously, because open touch point 406 extends outward from the smooth outer surface, it may be easily identified by the physician as the actuation point for opening arm 122, and may be easily actuated by a finger or thumb. Open touch point 406 may provide the additional benefit of being identified and actuated using only the physician's sense of touch. Because the physician may feel open touch point 406 as a projection outwards from the smooth outer surface, they may identify and actuate it without viewing it. This may reduce the time required to adjust the position of first lock 110 and/or second lock 112, and may additionally allow a simplified operation thereof.

Closed touch point 408 may include one or more protrusions extending radially outwards from outer surface 416. Closed touch point 408 may be positioned upon any desired portion of outer surface 416. In some embodiments, closed touch point 408 may include a plurality of protrusions which may be situated adjacent to a transition point between curved portion 412 and flat portion 414. In some embodiments, closed touch point 408 may be situated at a location which the physician can press with a finger to close arm 122. For example, when arm 122 is in the open position, the physician may identify closed touch point 408 and may press it with a finger to close arm 122 into the closed position. Advantageously, closed touch point 408 may be easily identified by the physician because it projects outward from outer surface 416. Additionally or alternatively, closed touch point 408 may include one or more divots and/or texture changes within outer surface 416 which may be felt and identified by the physician. Closed touch point 408 may also be identified and actuated using only the physician's sense of touch.

Figure 4B:
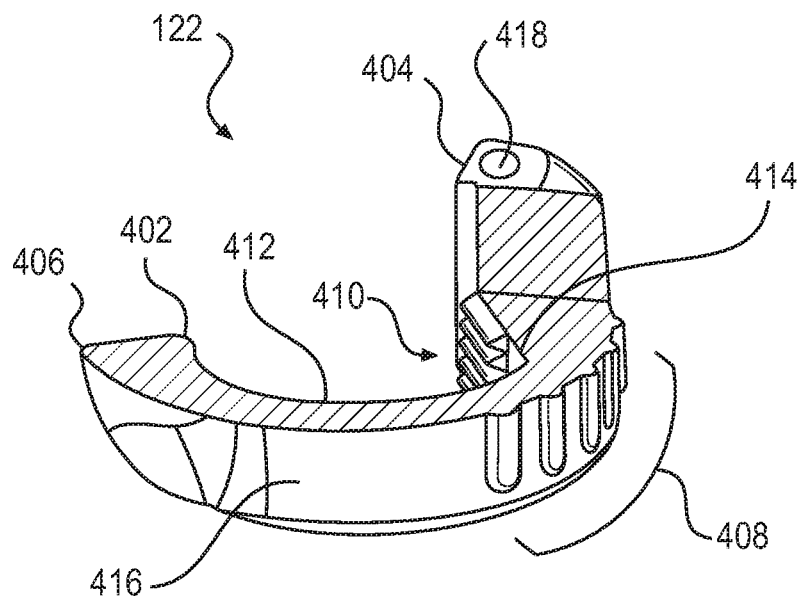
FIG. 4B is a partial perspective view of the exemplary arm of FIG. 4A, according to embodiments of the present disclosure.

FIG. 4B is a partial perspective view of exemplary arm 122. Arm 122 may be shaped to extend around body 120 at an angle greater than 180°. That is, arm 122 may be shaped to be situated within groove 308 when in the closed position and to extend circumferentially around more than half of intermediate portion 306.

FIGS. 5A-6B depict an exemplary adjustable lock in the closed position and in the open position. One of ordinary skill in the art will understand that one or more of first lock 110 and second lock 112 may assume the closed position and open position depicted in FIGS. 5A-6B.

Figure 5A:
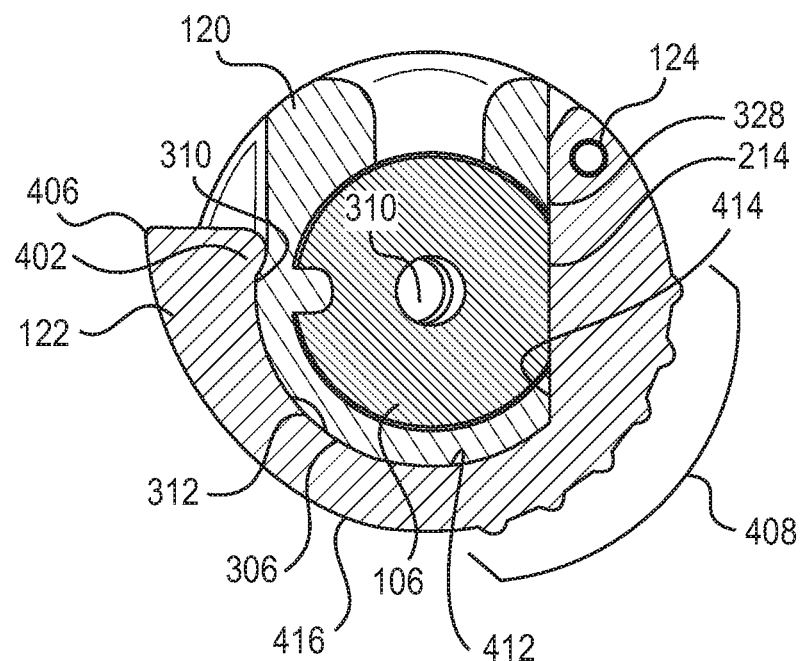
FIG. 5A is a cross-sectional view of an exemplary adjustable lock of the exemplary endoscopic accessory handle of FIG. 1A in a closed position, according to embodiments of the present disclosure.

FIG. 5A is a cross-sectional view of an exemplary adjustable lock in the closed position. In the closed position, arm 122 may be positioned within groove 308, with protrusion 402 positioned and retained within closed-position detent 310. Curved portion 412 may abut the outer wall of intermediate portion 306, while flat portion 414 may abut flat wall portion 328 and rail top surface 214. These abutments may prevent pivoting of arm 122 in a closing direction past the closed position. Outer surface 416 may form a smooth outer surface of the exemplary lock with the outer surfaces of proximal end portion 302 and distal end portion 304. Open touch point 406 and/or closed touch point 408 may extend radially outwards beyond the smooth outer surface. In some embodiments, the exemplary lock may be actuated by a single hand of the physician, who may actuate open touch point 406 with a finger or thumb to open arm 122 and may then use the same hand to adjust the position of the exemplary lock on rail 106. The smooth outer surface may provide the additional advantage of preventing unintentional opening of arm 122, as open touch point 406 may be the only easily-actuated feature extending from the smooth outer surface. The exemplary lock may have a low profile due to the smooth outer surface and due to the absence of any protruding features. This may minimize interference of the exemplary lock with the physician's hand during use.

Because arm 122 may be sized to extend circumferentially about more than half of intermediate portion 306, movement of arm 122 out of the closed position may cause elastic deformation of arm 122, resulting in a pinch force against body 120. Arm 122 may be relaxed when in the closed position. This may create resistance against movement of arm 122 out of the closed position, thus preventing unintentional opening of arm 122. Protrusion 402 may be retained within closed position detent 310 when in the closed position and within open position detent 312 when in the open position because removal of protrusion 402 out of the detents requires additional deformation of arm 122. In some embodiments, arm 122 may slide into the closed position if placed in a position intermediate to the open position and closed position. This may prevent arm 122 from remaining open longer than is necessary.

In some embodiments, placement of protrusion 402 into either of the closed position detent 310 and open position detent 312 may provide a clear tactile feel and an audible click. This may provide direct feedback to the physician when the desired arm position has been reached. This audible and tactile feedback may give confidence that the desired position of arm 122 has been reached, and may prevent the physician from wasting time verifying that arm 122 is in the correct position. In some embodiments, the presence of two detents may provide a clear binary indication of arm 122 being either open or securely closed. This may constitute an improvement over prior locks because there is no ambiguity as to whether the lock is open or closed.

Figure 5B:
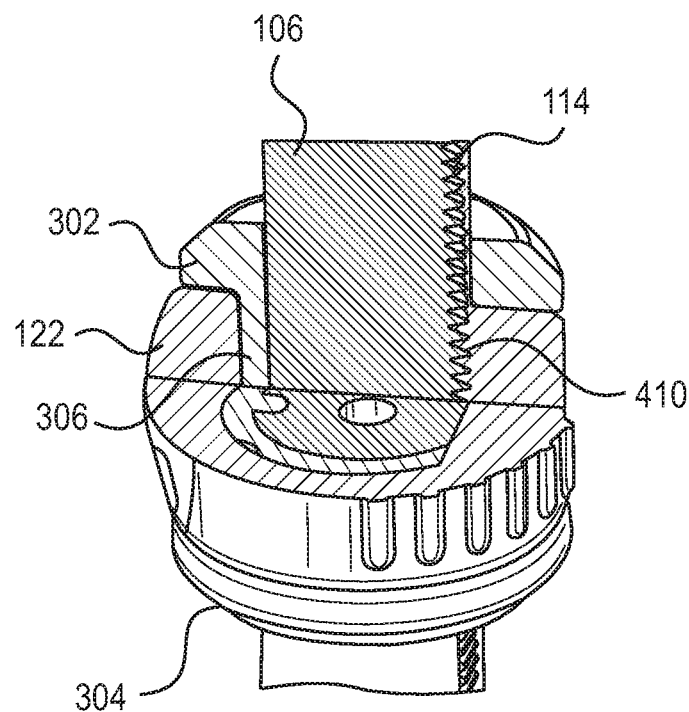
FIG. 5B is a partial perspective view of the exemplary adjustable lock of FIG. 5A in the closed position, according to embodiments of the present disclosure.

FIG. 5B is a partial perspective view of the exemplary lock in the closed position. Teeth 114 may extend through opening 320 to engage the teeth of toothed rack 114, thus securing lock 110 to rail 106. The engagement of the two sets of teeth may provide a strong connection that may withstand forces far beyond what is typical of endoscopic procedures. Due to the flush contact between the two sets of teeth and the shifting of the two sets of teeth during closing, all relative longitudinal movements may be prevented. Additionally, arm 122 may be shaped to eliminate clearance between body 120 and rail 106, thus preventing any side-to-side rattle. Arm 122 may eliminate clearance by shifting rail 106 during closing, pushing rail 106 to be flush with the inner surface of body 120 such that there is no gap between them. In some embodiments, teeth 114 may be slightly longer than the teeth of toothed rack 410; therefore, teeth 114 may push the teeth of toothed rack 410 during closing. In some alternative embodiments, the rack of teeth 114 and/or the inner surface of arm 122 may be shaped to protrude through opening 320 during closing to such an extent that they may push on rail 106 to eliminate rattle. The elimination of side-to-side rattle may provide a stronger and more stable connection between rail 106 and the exemplary lock.

Figure 6A:
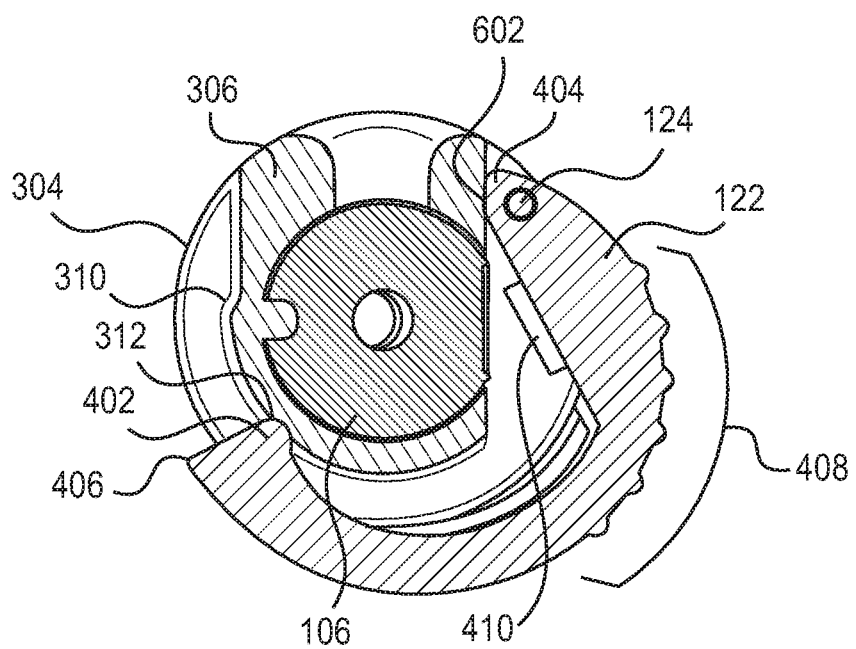
FIG. 6A is a cross-sectional view of the exemplary adjustable lock of FIG. 5A in an open position, according to embodiments of the present disclosure.

FIG. 6A is a cross-sectional view of the exemplary adjustable lock 110 in the open position. Protrusion 402 may be positioned and retained within open position detent 312 such that arm 122 is secured from unintended movement. When arm 122 is in the open position, hard stop 404 may contact a hard stop wall 602 of intermediate portion 306, preventing further pivoting of arm 122 in an opening direction past the open position. Alternatively, in some embodiments, hard stop 404 and hard stop wall 602 may come into contact when arm 122 pivots slightly beyond the open position in an opening direction.

When arm 122 is in the open position, flat portion 414 may be positioned away from rail 106 and body 120 such that teeth 410 are clear of the teeth of toothed rack 114. This clearance may allow lock 110 to slide along rail 106. However, even when arm 122 is in the open position, lock 110 still has a low profile because arm 122 only protrudes out slightly from lock 110. This may constitute an improvement over prior locks because lock 110 does not include any portion that protrudes outward in an inconvenient manner. As a result, a physician may hold accessory handle 100 in whichever position they desire because there are no portions of the exemplary lock around which they must position their hands.

Figure 6B:
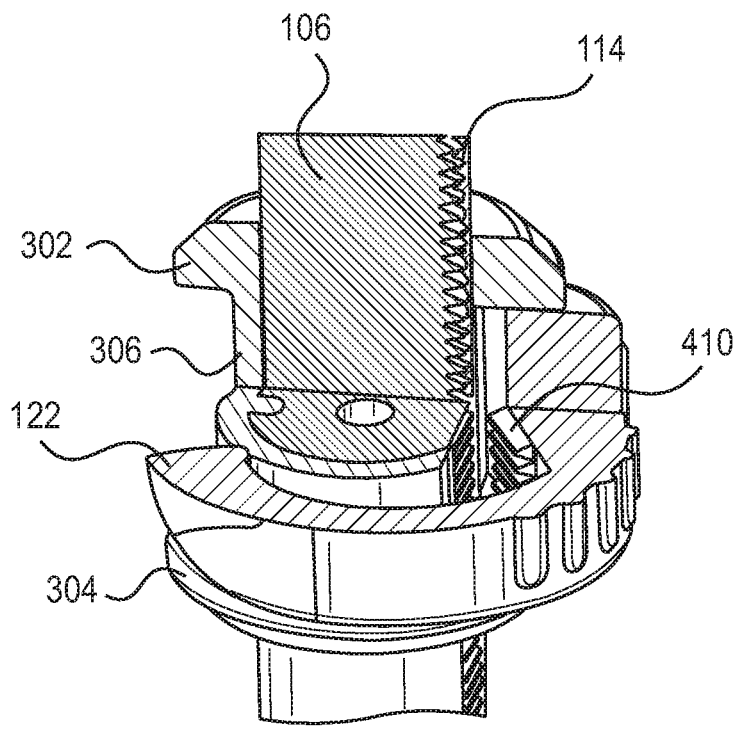
FIG. 6B is a partial perspective view of the exemplary adjustable lock of FIG. 6A in the open position, according to embodiments of the present disclosure.

FIG. 6B is a partial perspective view of the exemplary lock in the open position. When in the open position, teeth 410 may be positioned away from toothed rack 114 such that lock 110 may slide along rail 106, allowing the physician to adjust the axial position of lock 110.

Exemplary adjustable locks of the present disclosure may provide a number of benefits over prior locks, including prior endoscopic thumbscrew locks. In some embodiments, closed position detent 310 and open position detent 312 give a clear tactile feel and an audible click when they receive protrusion 402 in the closed or open position, respectively. This may give direct feedback to the physician that the desired open or closed position has been reached. This may remove ambiguity as to whether the lock is sufficiently closed to perform an endoscopic procedure with accessory handle 100. Additionally, lock 110 may be held and operated with one hand and has a low profile with no elements that protrude in an inconvenient fashion, even when in the open position. Further, teeth 410 and the teeth of toothed rack 114 are sized to allow fine adjustment of lock 110 relative to rail 106, as well as to shift axially relative to each other in the event of linear offset mismatch. However, the two sets of teeth also provide a strong connection which is capable of withstanding forces much greater than those typically generated during endoscopic procedures. Moreover, the interference fit between arm 122, body 120 and rail 106 eliminates any side-to-side rattle in the closed position, providing a secure and strong connection. In addition, lock 110 may have a reduced form factor and part count relative to prior devices, and may lower manufacturing costs due to the elimination of custom threaded metal parts.

The foregoing description has been presented for purposes of illustration. It is not exhaustive and is not limited to precise forms or embodiments disclosed. Modifications and adaptations of the embodiments will be apparent from consideration of the specification and practice of the disclosed embodiments. For example, the described implementations include hardware and software, but systems and methods consistent with the present disclosure can be implemented as hardware alone. In addition, while certain components have been described as being coupled to one another, such components may be integrated with one another or distributed in any suitable fashion.

Moreover, while illustrative embodiments have been described herein, the scope includes any and all embodiments having equivalent elements, modifications, omissions, combinations (e.g., of aspects across various embodiments), adaptations and/or alterations based on the present disclosure. The elements in the claims are to be interpreted broadly based on the language employed in the claims and not limited to examples described in the present specification or during the prosecution of the application, which examples are to be construed as nonexclusive. Further, the steps of the disclosed methods can be modified in any manner, including reordering steps and/or inserting or deleting steps.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and accordingly, all suitable modifications and equivalents may be resorted to, falling within the scope of the disclosure.

Other embodiments will be apparent from consideration of the specification and practice of the embodiments disclosed herein. It is intended that the specification and examples be considered as example only, with a true scope and spirit of the disclosed embodiments being indicated by the following claims.

What is claimed is:

1. An adjustable lock for an endoscopic accessory, the adjustable lock comprising:
   a body configured to be slidably mounted on a rail of the endoscopic accessory, the body having an open position detent in an outer surface thereof; and
   an arm extending about a portion of the body, the arm being connected to the body and pivotable relative to the body between a closed position and an open position, wherein an inner surface of the arm comprises:
   a protrusion situated on the inner surface, and
   teeth extending from the inner surface,
   wherein, in the closed position, the teeth of the arm are configured to engage a toothed rack of the rail, the toothed rack extending in a longitudinal direction of the rail, such that relative longitudinal movement between the lock and the rail is prevented, and
   wherein, in the open position, the arm is configured to extend away from the body such that the teeth of the arm are clear of teeth of the toothed rack, allowing the lock to slide relative to the rail, wherein when the arm is in the open position, the protrusion of the arm is retained within the open position detent of the body.

2. The adjustable lock of claim 1, wherein the arm is configured to elastically deform when the arm is in the open position and when the arm is in a position intermediate to the open position and the closed position.

3. The adjustable lock of claim 1, wherein when the arm is in the closed position, at least a portion of the inner surface of the arm is configured to contact at least a portion of the outer surface of the body such that the arm is prevented from pivoting further in a closing direction.

4. The adjustable lock of claim 1, further comprising:
   a second protrusion on the inner surface of the arm; and
   a closed position detent in the outer surface of the body, the open position detent and the closed position detent being situated at different portions of the outer surface of the body,
   wherein when the arm is in the closed position, the second protrusion is retained within the closed position detent.

5. The adjustable lock of claim 1, further comprising:
   a hard stop positioned on an end of the arm opposite from the protrusion, the hard stop configured to contact the body when the arm is in the open position and configured to prevent further pivoting of the arm in an opening direction.

6. The adjustable lock of claim 1, wherein the body further comprises:
   a pair of end portions, each of the end portions being disposed at a respective longitudinal end of the body; and
   a groove positioned between the end portions, wherein the groove is configured to receive the arm in the closed position.

7. The adjustable lock of claim 6, wherein an outer surface of the arm is configured to be substantially even with an outer surface of each of the end portions when the arm is in the closed position.

8. The adjustable lock of claim 7, further comprising:
   an open touch point situated on an end of the outer surface of the arm, the open touch point configured to extend radially outwards beyond the outer surface of each of the end portions when the arm is in the closed position.

9. The adjustable lock of claim 1, further comprising:
   a closed touch point situated on an outer surface of the arm, the closed touch point comprising at least one of a second protrusion, a divot, or a change in surface texture.

10. The adjustable lock of claim 1, wherein an end of the arm is pivotably connected to the body.

11. An endoscopic accessory comprising:
    a rail having a toothed rack extending in a longitudinal direction of the rail;
    a handle mounted upon a proximal end of the rail, the handle configured to connect to a tool; and
    a first adjustable lock comprising:
    a first body configured to be slidably mounted on the rail, and
    a first arm extending about a portion of the first body, the first arm being connected to the first body and pivotable relative to the first body between a closed position and an open position, wherein the first arm comprises teeth on an inner surface thereof, wherein, in the closed position, the teeth of the first arm are configured to engage teeth of the toothed rack such that relative longitudinal movement between the first lock and the rail is prevented, and wherein, in the open position:
- a first portion of the inner surface of the first arm is configured to extend away from the first body such that the teeth of the first arm are clear of the teeth of the toothed rack, allowing the first lock to slide relative to the rail, and
- a second portion of the inner surface of the first arm is configured to contact an outer surface of the first body such that the first arm is secured against pivoting relative to the first body.

12. The accessory of claim 11, wherein the handle is configured to slide relative to the rail between the proximal end of the rail and the first lock.

13. The accessory of claim 11, further comprising:
- a sheath length adjustment handle configured to be mounted upon a distal end of the rail; and
- a second adjustable lock attached to a proximal end of the sheath length adjustment handle, the second lock comprising:
  - a second body configured to be slidably mounted on the rail, and
  - a second arm extending about a portion of the second body, the second arm being connected to the second body and pivotable relative to the second body between a second closed position and a second open position, wherein the second arm comprises teeth on an inner surface thereof, wherein, in the second closed position, the teeth of the second arm are configured to engage the teeth of the toothed rack such that relative longitudinal movement between the second lock and the rail is prevented, and wherein, in the second open position:
- a first portion of the inner surface of the second arm is configured to extend away from the second body such that the teeth of the second arm are clear of the teeth of the toothed rack, allowing the second lock and the sheath length adjustment handle to slide relative to the rail, and
- a second portion of the inner surface of the second arm is configured to contact an outer surface of the second body such that the second arm is secured against pivoting relative to the second body and the sheath length adjustment handle.

14. The accessory of claim 13, wherein relative longitudinal movement between the second lock and the rail results in adjustment of the length of an exposed portion of a sheath extending distally from the sheath length adjustment handle.

15. The accessory of claim 14, wherein relative longitudinal movement between the handle and the rail results in adjustment of the length of an exposed portion of the tool extending distally from the sheath.

16. The accessory of claim 13, wherein the rail comprises:
- a barrier situated in a middle portion of the rail, wherein an outer surface of the barrier is smooth and is larger in diameter than inner surfaces of the first body and second body.

17. The accessory of claim 13, wherein when the second arm is in the second closed position, the teeth of the second arm are configured to extend radially inwards into a lumen of the second body and to push the rail to be positioned flush with the second body.

18. The accessory of claim 13, wherein the teeth of the second arm and the teeth of the toothed rack have the same pitch, the pitch being one tooth per a length of between 0.5 mm and 5 mm.

19. The accessory of claim 13, wherein the teeth of the first arm, the teeth of the second arm, and the teeth of the toothed rack are triangular.

20. The accessory of claim 13, wherein an end of the second arm is pivotably connected to the second body.

21. The accessory of claim 11, wherein when the first arm is in the closed position, the teeth of the first arm are configured to extend radially inwards into a lumen of the first body and to push the rail to be positioned flush with the first body.

22. The accessory of claim 11, wherein the teeth of the first arm and the teeth of the toothed rack have the same pitch, the pitch being one tooth per a length of between 0.5 mm and 5 mm.

23. The accessory of claim 11, wherein an end of the first arm is pivotably connected to the first body.

24. Means for adjustably locking to an endoscopic accessory, comprising:
- first means for sliding along a rail of the endoscopic accessory, the rail having teeth extending in the longitudinal direction thereof;
- second means for selectively engaging with the teeth of the rail; and
- third means for securing the second means against pivoting relative to the first means while the first means slides along the rail.

* * * * *